US00PP10528P

United States Patent [19]

Pouw

[11] Patent Number: Plant 10,528

[45] Date of Patent: Aug. 4, 1998

[54] HYBRID TEA ROSE PLANT NAMED 'RUIBIYEL'

[75] Inventor: A. A. Pouw, PL De Kwakel, Netherlands

[73] Assignee: De Ruiter's Nieuwe Rozen B.V., Pl De Kwakel, Netherlands

[21] Appl. No.: 789,832

[22] Filed: Jan. 28, 1997

[51] Int. Cl.[6] ..... A01H 5/00

[52] U.S. Cl. ..... Plt./12

[58] Field of Search ..... Plt./11, 12, 13

*Primary Examiner*—Howard J. Locker
*Attorney, Agent, or Firm*—Christie, Parker & Hale, LLP

[57] ABSTRACT

A new variety of hybrid tea rose plant producing pink and cream/white bicolor flowers of good form and suitable for growing under glass.

1 Drawing Sheet

BACKGROUND OF THE INVENTION

The present invention relates to a new and distant variety of rose plant of the hybrid tea rose class which was created by crossing undistributed, unnamed and unpatented seedlings as seed and pollen parents in De Kwakel, Holland. the varietal denomination of the new variety if 'Ruibiyel'. The new variety was isolated and asexually reproduced by budding in Holland.

SUMMARY OF THE INVENTION

Among the novel characteristics possessed by this new variety which distinguish it from its parents and all other varieties of which I am aware are its attractive pink and cream/white blend flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed.

The following further horticultural description is based on observations made of specimens grown under glass in De kwakel, Holland.

Flower

Blooming habit: Nearly continuous.

A. Bud:

(1) *Size.*—Medium, about 3 to 4 cm long and about 2 to 3 cm wide.

(2) *Form.*—Ovate (shape of longitudinal section just before separation of sepals); urn-shaped after sepals part.

(3) *Color.*—As sepals divide, near 16B to 16C with red edge, near 50A.

(4) *Sepals.*—Much longer than green bud, generally foliated; lower surface near 139C, upper surface near 138B.

(5) *Peduncle.*—Long, about 13 cm, Strength-erect, very strong. Color — near 147A to 147B.

B. Bloom:

*Flower*—Medium; viewed from above — star-shape; viewed from side — (a) upper part of fully opened flower, flattened convex; (b) lower part of fully opened flower, flat.

(1) *Size.*—Average size when fully expanded — about 10 to 12 cm.

(2) *Borne.*—Singly, one to a stem.

(3) *Form.*—Pointed center, exhibition type, spiral imbricated, outer petals reflex to points, inner petals roll under.

(4) *Petalage.*—Fully double, about 20, about 4 petaloids, petaloids crinkled.

(5) *Color.*—After sepals part and petals unfurl color of petal top surface is near 50B to 50C; color of petal undersurface is near 8D in ⅓ open flowers; showing clear bicoloration; as bloom opens petal top surface becomes near white but retains red coloration at reflexed points and at very edge; near 49C. Zone of petal attachment near 11C to 12C. Overall tonality from a distance is attractive pink and cream/white bicolor.

(6) *Peduncle.*—Generally smooth, few hairs or prickles.

(7) *Fragrance.*—Absent to weak.

(8) *Length of stem* *.—About 60 cm.

(9) *Production* *.—About 225/m$^2$/yr.

*Average only, depends on circumstances of cultivation.

Petals:

(1) *Texture.*—Crisp.

(2) *Appearance.*—Inside velvety and outside satiny.

(3) *Form and size.*—Broad, medium to large; outer petals reflex to points.

(4) *Arrangement.*—Regularly arranged, imbricated.

(5) *Petaloids.*—Several about 4.

(6) *Lasting quality.*—Long-lasting quality on plant and after cutting; vaselife about 18 days; blooms on plant last for about 20 days and then the petals drop; color fades after about 5 days.

Reproductive Organs

A. Stamens, filaments and anthers:

*Arrangement and color.*—Regularly arranged around styles; color of filaments — orange red.

B. Pollen:

*Color.*—Orange red.

C. Styles: Long, stigm above mouth of receptacle, yellow.

D. Stigmas: Yellow, positioned below anthers.

E. Hip: Funnel-shaped; medium seed vessel at petal fall, orange, about 2 cm.

Plant

A. Form: Narrow, bushy, average disease resistance, some susceptibility to mildew, about 1.6 m height and about 0.5 m width.

B. Growth: Vigorous.

C. Foliage: Compound 3, 5 and 7 leaflets.

(1) *Size.*—Small; about 12 to 15 cm.

(2) *Quantity.*—Abundant.

(3) *Color.*—Juvenile foliage — red purple to bronze-reddish brown; near 191B; weak anthocyanin coloration, (shoot about 20 cm long); upperside near 136A, underside near 137C.

(4) *Shape.*—Broad oval.

(5) *Texture.*—Upper side is medium glossy; underside is matte.

(6) *Edge.*—Serrate.

(7) *Serration.*—Ordinary, acuminate apices.

(8) *Leaf stem.*—Color — near 147B to 147C.

(9) *Stipules.*—Long, simple, medium green, distinct auricle.

(10) *Leaflets.*—Cross section — slight concave: weak undulation of margin; terminal leaflet — short length and narrow width; blade about 4 to 6 cm long and 4 to 5 cm wide, rounded base.

D. Wood:

(1) *New wood.*—Color — young shoots have weak to medium anthocyanin; coloration — bronze red purple to reddish brown.

(2) *Old wood.*—Color — medium green, near 147A to 147C.

E. Prickles (thorns):

(1) *Prickles.*—Present; quantity (main stalk) — ordinary; shape of lower side — concave; Length — short prickles absent or very few, long prickles medium; Color — near 159A; Position — irregular.

What is claimed is:

1. A new and distinct variety of rose plant of the hybrid tea rose class substantially as shown and described.

* * * * *

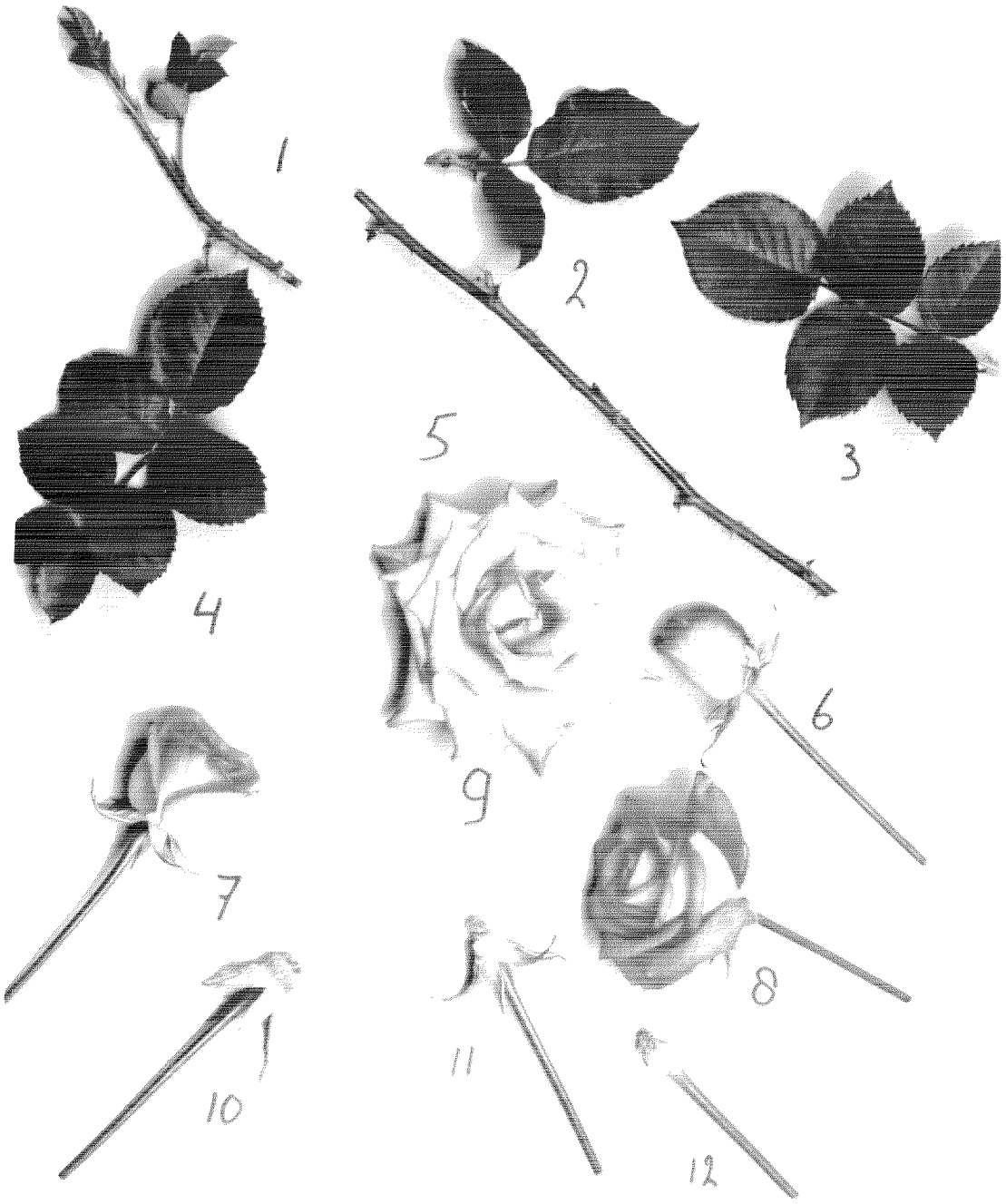
1
2
3
4
5
6
7
8
9
10
11
12

UNITED STATES PATENT AND TRADEMARK OFFICE

CERTIFICATE OF CORRECTION

PATENT NO. : Plant 10,528
DATED : August 4, 1998
INVENTOR(S) : A.A. Pouw

It is certified that error appears in the above-identified patent and that said Letters Patent is hereby corrected as shown below:

Column 1, line 6, change "variety if" to -- variety is--.
Column 2, lines 7,8, change "De kwakel, Holland" to
-- De Kwakel, Holland --.

Column 3, line 21, change "stigm" to --stigma--.
Column 3, line 32, delete "Small;".

Signed and Sealed this

Fifteenth Day of June, 1999

*Attest:*

Q. TODD DICKINSON

*Attesting Officer*

*Acting Commissioner of Patents and Trademarks*